United States Patent [19]
Santini

[11] Patent Number: 4,623,955
[45] Date of Patent: Nov. 18, 1986

[54] ANO-GENITAL SELF-VIEWING DEVICE

[76] Inventor: Luis A. Santini, Suite 3F, Condominium Las Torres Sur, Bayamon, P.R. 00619

[21] Appl. No.: 665,587

[22] Filed: Oct. 29, 1984

[51] Int. Cl.⁴ ............................................. F21V 33/00
[52] U.S. Cl. ................................... 362/135; 362/139; 128/22; 4/661; 350/616; 350/631
[58] Field of Search ............... 362/135, 138, 139, 142, 362/154, 157, 200, 217, 260, 277, 296, 341; 350/612, 616, 617, 613, 621, 623, 626, 631, 632, 636; 4/661; 128/22, 21; 248/466, 476, 479, 488

[56] References Cited

U.S. PATENT DOCUMENTS

| | | | |
|---|---|---|---|
| 1,334,810 | 3/1920 | Smith | 350/616 |
| 2,598,291 | 5/1952 | O'Brien | 362/139 X |
| 3,310,359 | 3/1967 | Linke | 350/616 |
| 3,775,777 | 12/1973 | Roberts, Jr. | 4/661 |
| 3,989,359 | 11/1976 | Shutt | 350/631 |
| 4,314,314 | 2/1982 | Hubner | 362/135 X |
| 4,432,043 | 2/1984 | Yuen | 362/200 X |

*Primary Examiner*—Willis R. Wolfe, Jr.
*Attorney, Agent, or Firm*—Garrison & Stratton

[57] ABSTRACT

The ano-genital self-viewing device is used in conjunction with a conventional toilet to permit a person to conveniently view his or her own ano-genital region while seated in the conventional manner. The device has a fluorescent lamp with batteries, supporting arms to contain the device below the user and mirrors, one planar to reflect normal images and another concave to reflect magnified images from the illuminated ano-genital region upwards. The arms and mirrors fold compactly onto the base of the device to facilitate transportation and storage.

11 Claims, 8 Drawing Figures

U.S. Patent  Nov. 18, 1986  Sheet 1 of 2  4,623,955
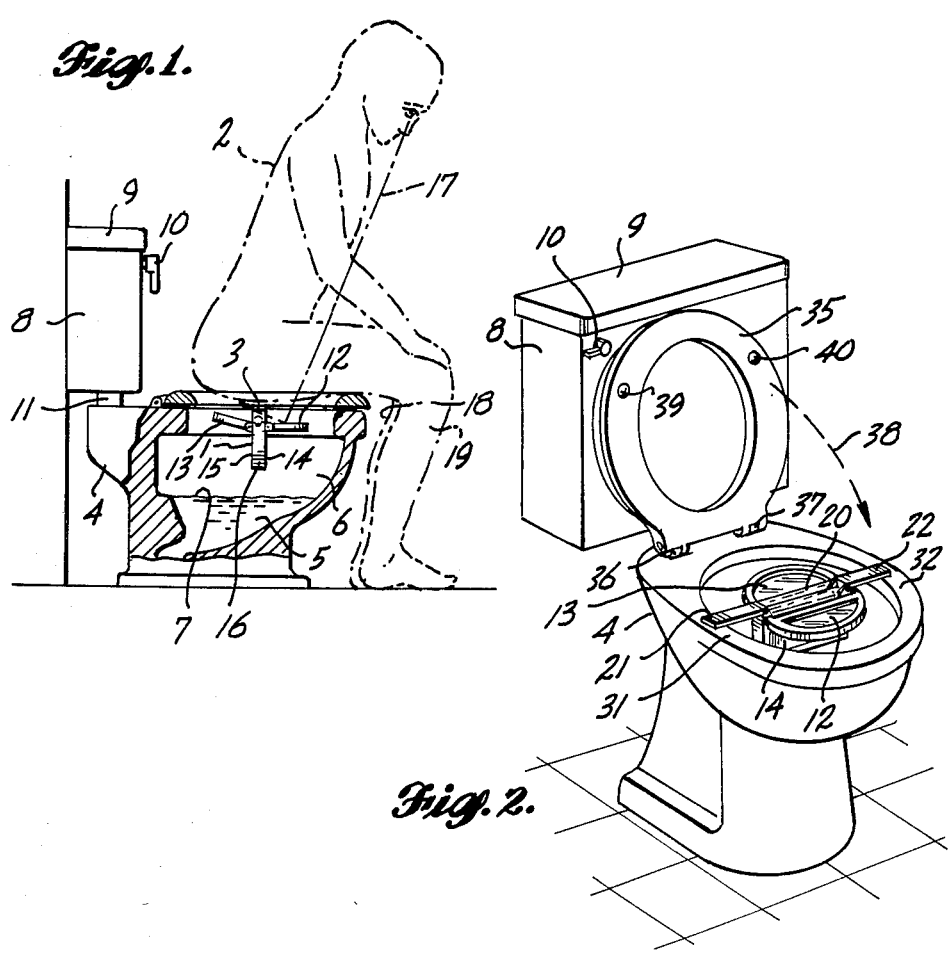
Fig. 1.
Fig. 2.
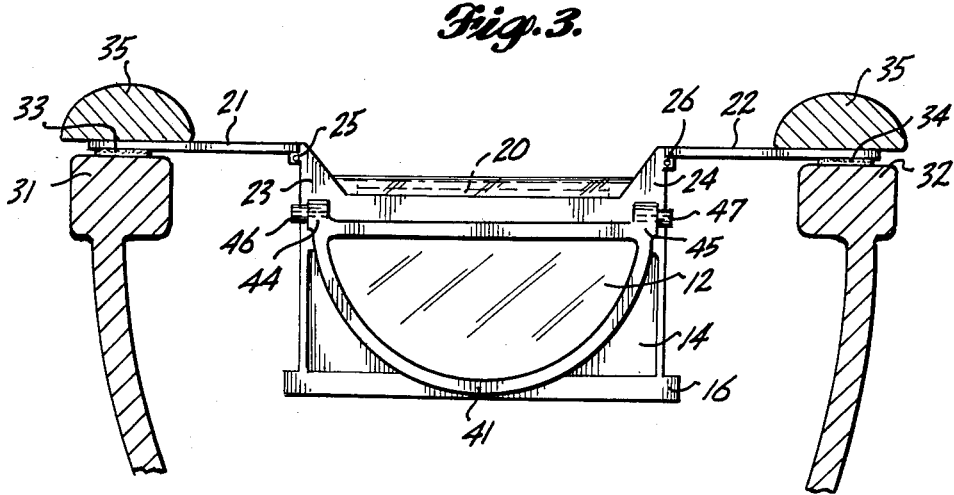
Fig. 3.

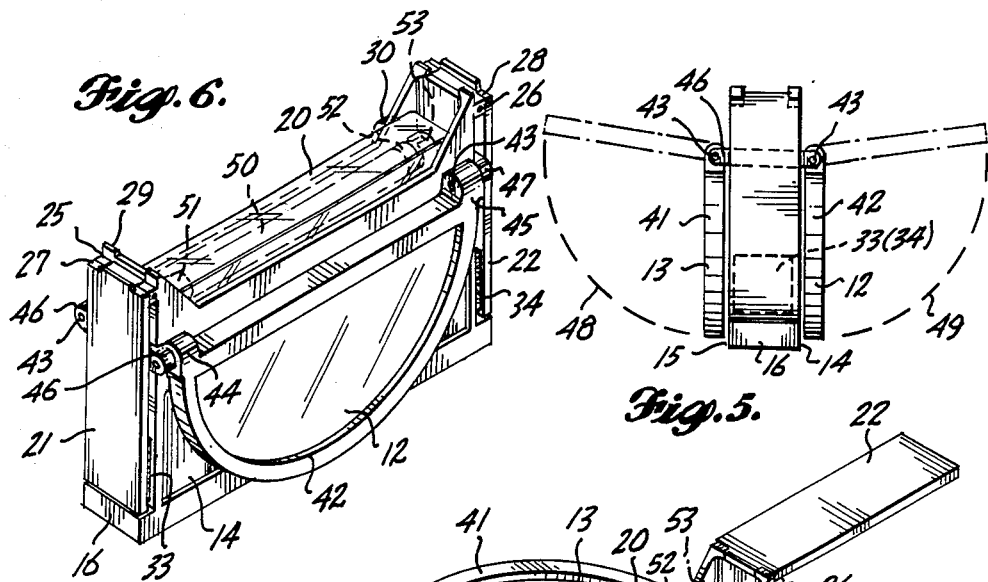

ANO-GENITAL SELF-VIEWING DEVICE

FIELD OF THE INVENTION

This invention relates to an illuminating optical system and in particular to an illuminating reflection system for self observation; more particularly, this invention relates to an illuminating reflecting apparatus with support means to be fitted inside a toilet below the user and above the waste receptacle area to permit a person to conveniently view his or her own ano-genital region while seated on the toilet in the conventional position.

BACKGROUND OF THE INVENTION

Everyone should have his or her ano-genital region visually inspected periodically for signs of disease, medical disorders, for personal hygene and other reasons. The ano-genital region generally includes the region of the human body between the thighs where the digestion, excretory and reproductive systems end, specifically, the region includes the anus, perineum and sexual organs. This important, but often neglected, area of the human body is susceptible to disease many of which are sexually transmitted.

It is well known that sexually transmitted diseases have increased to the point that many authorities consider them to be at epidemic levels. Most of these diseases can be diagnosed by visible inspection of the ano-genital area.

Genital herpes is the most frequent sexually transmitted disease in the world, if one takes into account its recurrences. Unfortunately, it has no cure. It is estimated that about a half million individuals in the United States acquire herpes annually. This disease is caused by an infection of the lower genital tract caused by the herpes simplex virus, type II. Commonly called herpes, the first signs or symptoms are a diffused swelling of the lymph glands mainly in the genital-groin area, followed by pain and a burning or itching sensation. Fever, headache and general malaise may accompany the initial infection in particular, which is usually the worst of all subsequent, recurrent infections. Women may experience an increase in vaginal discharge, and men might note a watery urethral discharge. Urination may become quite frequent and urgent. In women, the next stage of development encompasses the appearance of small sores in a patch-like formation on the labia, clitoris, vaginal wall or opening, cervix, perineum, bottocks, thighs or anus.

The rash and blisters become extremely itchy and annoying and may bleed or secrete fluid. They eventually scab over and disappear after the 7th to 10th day.

Herpes genitalis infection in the female creates grave health problems. If there is evidence of active infection within 2 to 4 weeks of predicted delivery, cesarean section should be entertained as the optimum method of delivery. The incidence of cervical uterine cancer is increased sevenfold in women with herpes genitalis.

Although sub-acute herpetic lesions can be asymptomatic physical and sexual contact should be avoided during the time herptic signs are visible.

Syphilis is caused by bacteria and forms an ulser at the point where the bacteria enters the body, commonly in the ano-genital area. In the primary stage, these sores are open and are often painless at times so small that they may go undetected unless this area is visually examined closely and regularly. Early visible detection of these sores is extremely important for its treatment and isolation to prevent transmission to others.

Venereal warts are caused by a virus and often forms painless lesions in the perineum. The warts are characterized by a rough warty area on the perineum and and area around the vagina. These warts are quite small when they first appear, and can easily go undetected until they become so numerous and large that they begin to interfere with urination, defecation and intercourse. Early visible detection is essential for adequate treatment.

It is estimated that nearly half of the population suffers from hemorrhoids by the age of 50. The suffering from hemorrhoids can be greatly reduced by the application of topical ointments of the affected parts. These treatments are best done while viewing the area.

Approximately a half million women undergo an episiotomy during normal vaginal delivery and most of them would like to see how well their incision was sutured.

A host of other diseases and ailments commonly affecting the ano-genital region are easily diagnosed by visual inspection.

Unfortunately, the human body does not permit a person to visually inspect his or her own ano-genital region comfortably. Thus, humans must usually rely upon others to make close visual observations of the ano-genital region. Additionally, in ours as well as many other societies, the ano-genital area of the human body is subject to special social taboos and prohibitions. Because of this and despite the need for frequent visual inspection, very few people have this area of the body looked at unless it is done by a medical specialist responding to some specific medical reason or in the course of a general physical.

It is obvious that a very large number of individuals would like to inspect their ano-genital region with ease, comfort, privacy and clarity.

An objective of this invention is to provide for a simple, self-contained apparatus to facilitate a person to inspect one's self in the ano-genital region.

BACKGROUND OF THE INVENTION

In the generic sense, a toilet is an apparatus incorporating a seating feature with a void thereunder to permit a seated user to releave him or herself and to provide a convenient access to the user's ano-genital area for hygenic purposes. Although there are many kinds of toilets, the most common known toilets are the bidet, bedpan, water closet, chemical toilet and rustic supporting structure set upon a simple composting pool or pit. In the present world, the commonly used toilet seems to be the water flushable toilet bowl with a flat circular or oval rim. Often, the bowl also features a flat bottom seat with a curved seat surface to facilitate an undressed seated user. Often the seat also has supporting spacers attached to its under surface while the rear portion of the seat is attached by hinges to near the rear of the rim. The seat can thus be rotated down to rest upon the rim of the bowl providing a comfortable opportunity to a seated user, while permitting the seat to be rotated up off the rim in order to permit a man to urinate in a standing position without fear of splashing the seat surface.

SUMMARY OF THE INVENTION

The objects and advantages of this invention are obtained by combining into a device a reflective means, self-contained illuminating source and foldable support members, arranged to hold the device inside a toilet centrally positioned under the user. Positioned correctly, the light source illuminates upward towards the ano-genital region of the user while the reflective means positioned forward of the light source reflects the illuminated image upwards through the opened legs of the user seated on the toilet in the conventional manner. Thus, by merely looking downwards through his or her legs, the user can view his or her illuminated ano-genital region. By incorporating a concave mirror, the virtual image of the ano-genital region can also be magnified providing an equivalent close-up view of the illuminated ano-genital region.

The fact that almost everybody has ready access to a toilet makes this device particularly advantageous since the device is to be used in conjunction with a universally available facility. Although the device has advantages when used with a toilet seat, it is apparent that the device can also be used in conjunction with any toilet upon which a user sits. Similarly, the device can also be used in circumstances where a toilet is unavailable by resting the device upright upon its base on the floor while the user squats undressed thereabove.

Of importance in this invention, is the concept that the mirrors are adjustably hinged onto the forward and rear faces while the support members or arms are hinged with locking means to the side faces of the base. When the mirrors and side arms are folded to a closed position the device is kept small and elegant in its dimensions. Accordingly, it is of significance that the volume of the closed device is compact and is ideal for travel and storage when not in use.

Underlying the instant invention requires an appreciation of the fact that the illuminated means is to be located very close to extremely sensitive organs of the human body. For this reason, it is important that the operation of the illuminating means be of low operating temperature to permit extended operation without producing discomfort or danger of burns. In addition, it can be appreciated that in general, only a moderate lightness, without glare, is sufficient to illuminate in detail the object to be viewed such as the ano-genital region. For an illuminating source, it is preferred to have a non-point illuminating means to reduce shadows and to provide a more homogeneous illumination of the ano-genital region. Accordingly it is a further feature of this invention to incorporate the use of a centrally arranged, matted frosting or translucent florescent tube as the illuminating means.

A further feature of this invention lies in the fact that the illuminating means is modeled from one of the many small, compact battery operated florescent type lamps now commercially available; complete with its own case, mini-florescent lamp bulb with transparent protective cover, battery assembly, electronic activating means and on-off switch. An example of a model available with these features is the Mini-Florescent Lamp available from Radio Shack, a division of Tandy Corporation, Fort Worth, Tex. 96102, Catalog No. 61-2733.

Thus, the base of the invention can be designed to incorporate the use of a commonly available florescent lamp as its illuminating means.

An important additional feature of the invention rests upon the fact that there are no external electrical cords or cables connecting the device; the light source is entirely self-contained with its own power supply, an advantage for reasons of personal safety as well as convenience. The device need not be used only in conjunction with toilets which are near electric power outlets.

Further objectives and advantages of my invention will become apparent from a consideration of the drawings and ensuing description thereof.

BRIEF DESCRIPTION OF THE DRAWINGS

FIG. 1 is a cross-sectional side view of the ano-genital self-viewing device disclosing the relationship of the device with respect to a toilet and seated user.

FIG. 2 is a perspective view of the device indicating the manner in which the device is installed into the toilet.

FIG. 3 is an enlarged cross-sectional front view of the device used in conjunction with a toilet.

FIG. 4 is a perspective view of the device with the mirrors fully rotated outward and the side arms rotated, ready for use.

FIG. 5 is a side view of the device indicating the rotation mode of the mirrors.

FIG. 6 is the same perspective view as shown in FIG. 4 with the mirrors and side arms folded closed for compactness.

FIG. 7 is a top view of the device as shown in FIG. 6.

FIG. 8 is a front view of the device with a portion of the forward-rear face of the base and mirror removed to disclose some of the elements of this invention.

DETAILED DESCRIPTION OF THE INVENTION

Referring now to the drawings and more particularly to FIG. 1, an ano-genital self-viewing device is shown generally designated 1 which permits a person 2 to conveniently self-view his or her ano-genital region generally designated 3 while seated in the conventional position upon a toilet generally designated as 4.

While the preferred embodiment of this device can be used in conjunction with any toilet, the device herein shown is used in conjunction with conventional water flushable toilet bowl having a waste receptical area containing water 5 and a void area 6 above the high water line shown by line 7. The toilet 4 generally has a water storage tank 8 containing water (not shown) with a removable cover 9 and flushing means 10 which initiates a flow of water from the water storage tank 8 through a conduct 11.

The preferred embodiment of the device has two mirrors 12 and 13 each attached to a corresponding forward-rear face 14 and 15 of the base 16. Because of symmetry, the device may be installed into the toilet with either mirror 12 or 13 forward of the base with respect to the person seated upon the toilet. The preferred embodiment uses a concave reflective surface for one mirror to produce magnified images of the ano-genital area while the other mirror has a plane reflective surface to produce undistorted images. It does not matter which mirror uses which type of reflective surface since the device can be installed into the toilet with either mirror positioned forward of the seated user.

While seated in the conventional manner, the person merely looks downward approximately along the line of sight designated as 17, through his or her separated legs 18 and 19 into the forward placed mirror 12 in order to see an illuminated reflected image of his or her own ano-genital area 3.

The device is suspended with the illuminating means 20 upright within the toilet 4 by supporting means having two elongated members or arms 21 and 22 best shown in FIGS. 2, 3, 4, and 6. Each arm is attached at one of its ends to the upper edge of a side face 23 and 24 with 90 degree (90°) pin hinges 25 and 26 which permit the arms to fold against the side face as demonstrated in FIG. 6 or rotatively extended to the fully extended position demonstrated in FIGS. 2, 3, and 4 with each arm locked from further rotation by the attached ends of each arm 27 and 28 impinging upon corresponding surfaces of the upper edges of the side surfaces 29 and 30. The other ends of each arm 21 and 22 rest upon the upper side surfaces of the toilet bowl 31 and 32 through cushion means or pads 33 and 34.

Also shown in FIG. 2 is a toilet seat 35 attached to the area of the rear of the toilet bowl rim by two hinges 36 and 37 which permit the seat 35 to be rotated towards the toilet bowl through an arc designated by the dotted line 38 to rest upon two bottom surface spacers generally designated at 39 and 40. The pads 33 and 34 provide a resilience to protect the upperside surfaces of the toilet bowl and the arms in the event that the bottom surface spacers 39 and 40 are too short or are not installed.

Each mirror 12 and 13 of the preferred embodiment is held by a D-shaped molded mirror frame 41 and 42 which is attached at a forward-rear face of the device by tight fitting pins 43 which emerge from the ends of the D-frame 44 and 45 through matching bores of the hinge extension 46 and 47. Either frame with mirror can be rotated against the forward-rear face as is shown in FIG. 6 or opened as is described by lines 48 and 49 in FIG. 5 to the angle required by the user as shown in FIG. 1.

FIGS. 6 and 7 disclose the device folded into a compact unit suitable for travel or storage while FIG. 5 discloses the device ready for installation inside a toilet as described above.

The illuminating means of the preferred embodiment is a linear matted frosting or tubular translucent florescent lamp bulb 50, extending from nearly one side of the device to the other from electrical connections 51 and 52 at the ends of their bulb to matching electrical sockets 53 and 54, within a recess of the top face of the base containing the florescent lamp bulb 50 and electrical connections 51, 52 and sockets 53 and 54. In the preferred embodiment, the transparent cover 55 is made from a molded styrene-like material.

Referring now to FIG. 8, a portion of a forward-rear face and mirror is removed to show the locations of the electricity storage assembly generally shown as 56, electronic means 57, means to conduct by conducting helical wound springs 58, wires 59 and metallic strips 60. An on-off sliding switch 61 controls the illuminating state of the florescent lamp 50 by interrupting the flow of electricity. In the preferred embodiment, the storage assembly 56 is composed of 5 size "C" batteries 62 aligned in electrical series with each other to the electronic means 57. The individual components of the electronic means 57 required to convert the stored electricity of the storage assembly 56 to the requisite potential to power the florescent lamp bulb 50 into an illuminating state is well known in that art, and is shown here as an electronic assemblage of electronic components described herein as electronic means 57 without individualizing each and every component with its electrical function.

In describing the invention, reference has been made to a preferred embodiment. Those skilled in the art, however, and familiar with the disclosure of the subject invention, may recognize additions, deletions, modifications, substitutions and/or other changes which will fall within the purview of the invention as defined in the following claims.

What is claimed is:

1. An ano-genital self-viewing device particularly adapted to be used in conjunction with a toilet comprising:
   reflective means for viewing virtual images of the ano-genital region of a person seated on the toilet;
   means for illuminating the ano-genital region;
   means to support the device to the toilet so that said reflective means and illuminating means are positioned generally below the ano-genital region.

2. An ano-genital self-viewing device particularly adapted to be used in conjunction with a toilet comprising:
   reflective means for viewing virtual images of the ano-genital region of a person seated on the toilet;
   means for illuminating the ano-genital region;
   a base with a top face, two forward-rear faces and two side faces, each side face having an upper edge;
   a pair of elongated members, each member attached by one end to the upper edge of the corresponding side face with a free end of each member extending therefrom to above an upper side surface of the toilet permitting the device to rest by said members inside the toilet, whereby said reflective means and illuminating means are positioned generally below the ano-genital region of said person seated on the toilet.

3. The device as defined in claim 2 further comprising; rotative attachment means for attaching each elongated member at the one end to the upper edge of the corresponding side face permitting each member to be rotated against the corresponding side face of the base for compactness; and,
   locking means to prevent the members from rotating through its extended position.

4. The device as defined in claim 2 or 3 additionally comprising:
   cushion means attached to a bottom surface of the free end of each member, the cushion means providing resilient embracing of the free end of each member to the upper side surface of the toilet whenever a toilet seat impinges upon said members.

5. The device as defined in claim 2 wherein said illuminating means includes
   a florescent lamp bulb mounted on the top face;
   electricity storage assembly;
   electronic means to convert electricity at its storage assembly potential to the requisite potential to power said florescent lamp bulb into an illuminating state;
   means to conduct the stored electricity from the electricity storage assembly to and through said electronic means and florescent lamp bulb;
   on-off switch to interrupt the conduction of the electricity whenever desired.

6. The device as defined in claim 5 wherein said florescent lamp bulb is linear and mounted along the top face of the base so that its central axis extends from nearly one side to the other side.

7. The device as defined in claim 5 or 6 wherein a transparent cover encloses the top face over the florescent lamp bulb and conducting means.

8. The device as defined in claim 2 wherein said reflective means includes
   at least one mirror with at least one reflective surface attached to one of the forward-rear faces of the base;
   adjustment means to permit the person to make and maintain angular changes of the reflective surface with respect to the attached forward-rear face of the base.

9. The device as defined in claim 8 wherein the mirror is rotatively attached to one of the forward-rear faces of the base permitting said mirror to be rotated against the attached forward-rear face when not in use.

10. The device as defined in claim 8 or 9 wherein said reflective surface is planar.

11. The device as defined in claim 8 or 9 wherein said reflective surface is concave.

* * * * *